US011369748B2

(12) United States Patent
Grubbe (10) Patent No.: US 11,369,748 B2
(45) Date of Patent: Jun. 28, 2022

(54) DRUG INJECTION DEVICE WITH DEFLECTABLE TRANSDUCERS

(71) Applicant: Novo Nordisk A/S, Bagsvaerd (DK)

(72) Inventor: Mikkel Schouenborg Grubbe, Hilleroed (DK)

(73) Assignee: Novo Nordisk A/S, Bagsvaerd (DK)

( * ) Notice: Subject to any disclaimer, the term of this patent is extended or adjusted under 35 U.S.C. 154(b) by 257 days.

(21) Appl. No.: 16/769,644

(22) PCT Filed: Dec. 4, 2018

(86) PCT No.: PCT/EP2018/083550
§ 371 (c)(1),
(2) Date: Jun. 4, 2020

(87) PCT Pub. No.: WO2019/110618
PCT Pub. Date: Jun. 13, 2019

(65) Prior Publication Data
US 2021/0162136 A1    Jun. 3, 2021

(30) Foreign Application Priority Data

Dec. 4, 2017 (EP) .................................... 17205309

(51) Int. Cl.
*A61M 5/315* (2006.01)
*A61M 5/31* (2006.01)

(52) U.S. Cl.
CPC .... *A61M 5/31593* (2013.01); *A61M 5/31583* (2013.01); *A61M 2005/3126* (2013.01);
(Continued)

(58) Field of Classification Search
CPC .......... A61M 5/31593; A61M 5/31583; A61M 2005/3126; A61M 2205/0294; A61M 2205/3327; A61M 2205/581
See application file for complete search history.

(56) References Cited

U.S. PATENT DOCUMENTS 4,853,580 A    8/1989 Sula
6,277,099 B1   8/2001 Strowe et al.
(Continued)

FOREIGN PATENT DOCUMENTS

CN    103167887 A    6/2013
CN    105102038 A    11/2015
(Continued)

*Primary Examiner* — Dung T Ulsh
(74) *Attorney, Agent, or Firm* — Wesley Nicolas (57) ABSTRACT

The present invention provides a drug injection device (100) comprising a first element (140) and a second element (103) configured to undergo unidirectional movement relative to each other corresponding to an action performed on or by the drug injection device (100), wherein the first element (140) comprises a plurality of serially disposed protrusions (143), wherein the second element (103) comprises first and second deflectable transducers (103a/153a, 103b/153b) configured for sequentially cooperating with the plurality of protrusions (143), and wherein a processor (151) is electrically connected with the first and second deflectable transducers (103a/153a, 103b/153b) to register activation signals, wherein the protrusion configuration is so disposed on the first element (140) and the first and second deflectable transducers (103a/153a, 103b/153b) are so disposed on the second element (103) that a second activation signal generated by the second deflectable transducer (103b/153b) is delayed relative to a first activation signal generated by the first deflectable transducer (103a/153a) as the first element (140) and the second element (103) move relative to each other, and wherein the processor (151) is configured to provide a) a first control action if a time delay between the first and second activation signals is above or equal to a pre-defined value, and b) a second control action if said time delay is below said pre-defined value.

15 Claims, 8 Drawing Sheets

(52) U.S. Cl.
CPC ............... *A61M 2205/0294* (2013.01); *A61M 2205/3327* (2013.01); *A61M 2205/581* (2013.01)

(56) References Cited

U.S. PATENT DOCUMENTS

| | | | |
|---|---|---|---|
| 8,217,808 | B2 | 7/2012 | Fazilleau et al. |
| 10,213,560 | B2 | 2/2019 | Butler et al. |
| 10,682,467 | B2 | 6/2020 | Avery et al. |
| 10,744,270 | B2 | 8/2020 | Avery |
| 2006/0202681 | A1 | 9/2006 | Shoji |
| 2007/0135756 | A1 | 6/2007 | Kohlbrenner et al. |
| 2013/0079727 | A1 | 3/2013 | Schildt et al. |
| 2013/0218093 | A1 | 8/2013 | Markussen et al. |
| 2015/0302818 | A1* | 10/2015 | Cowe ................ G09G 5/00 345/440.2 |
| 2016/0263327 | A1* | 9/2016 | Radmer ................ A61M 5/20 |
| 2018/0169345 | A1* | 6/2018 | Stephenson ....... A61M 5/31551 |
| 2019/0125977 | A1* | 5/2019 | Wang ................ A61M 5/31551 |
| 2019/0217014 | A1* | 7/2019 | Davies ................ G06M 1/042 |
| 2019/0366009 | A1* | 12/2019 | Hewson ............ A61M 5/31583 |

FOREIGN PATENT DOCUMENTS

| | | |
|---|---|---|
| CN | 107106781 A | 8/2017 |
| CN | 107206178 A | 9/2017 |
| EP | 282884 A2 | 9/1988 |
| EP | 1547907 A1 | 6/2005 |
| EP | 1804868 | 12/2009 |
| EP | 3068468 A1 | 9/2016 |
| EP | 3400981 B1 | 12/2019 |
| GB | 1219757 A | 1/1971 |
| WO | 2006/045525 | 5/2006 |
| WO | 2006045523 A1 | 5/2006 |
| WO | 2015/071354 | 5/2015 |
| WO | 2015071354 A1 | 5/2015 |
| WO | 2017013464 | 1/2017 |

* cited by examiner

Prior art

Prior art

Fig. 9

DRUG INJECTION DEVICE WITH DEFLECTABLE TRANSDUCERS

CROSS-REFERENCE TO RELATED APPLICATIONS

This application is a 35 U.S.C. § 371 National Stage application of International Application PCT/EP2018/083550 (published as WO 2019/110618), filed Dec. 4, 2018, which claims priority to European Patent Application 17205309.2, filed Dec. 4, 2017; the contents of which are incorporated herein by reference.

FIELD OF THE INVENTION

The present invention relates generally to devices for delivering medicine to a subject, and more specifically to injection devices capable of expelling one or more doses of drug from a drug reservoir.

BACKGROUND OF THE INVENTION

In the diabetes care segment parenteral drug administration carried out using a traditional vial and syringe system is increasingly being substituted by administration using a pen injection device. Pen injection devices are particularly convenient in that they allow the user to perform a dosed injection from a prefilled drug reservoir without first having to manually transfer the particular dose from one reservoir (the vial) to another (the syringe).

Predominantly, two types of pen injection devices are available, durable injection devices being capable of delivering one or more doses of drug from a prefilled drug cartridge which can be loaded into the device before use and replaced after exhaustion, and disposable injection devices being capable of delivering one or more doses of drug from a prefilled and non-exchangeable drug cartridge. Each of these types of pen injection devices are, or may in principle be, realised in various sub-types, such as e.g. single shot devices adapted to deliver only one dose from a drug cartridge, multi-shot devices capable of delivering a plurality of doses from a drug cartridge, manual devices, where the user provides the force needed for injection, automatic devices having a built-in energy source releasable to occasion the injection, fixed dose devices adapted to deliver a predetermined dose of drug, variable dose devices offering delivery of different doses of drug, settable by the user, etc.

As the labels suggest a durable injection device is intended for use over a considerable period of time during which multiple drug cartridges are exhausted and replaced, whereas a disposable injection device is intended for use until its dedicated drug cartridge is exhausted, after which the entire injection device is discarded.

In the treatment of diabetes it is advisable to keep a log of the administered doses of a particular drug (e.g. insulin or glp-1), as well as the respective times of dose administration. Some injection devices accordingly offer electronic dose capturing and the opportunity to review dose related information on a digital display.

As an example, U.S. Pat. No. 6,277,099 B1 (Becton, Dickinson and Company) discloses an electronic medication delivery pen, wherein a dialled dose is detected by a piezoelectric sensor arrangement, activated in response to rotation of a user manipulable dose knob, and displayed on a liquid crystal display. The medication delivery pen also comprises a memory function, which together with the liquid crystal display provides an operable interface for conveying the dose size and the time of the last five injections.

US 2015/0302818 A1 (Owen Mumford Limited) discloses the use of an electronic paper display device in addition to a conventional scale drum merely to enable dose display of a larger font size. The electronic display is driven by signals from piezoelectric elements which are successively energised during rotation of a dose setting knob.

Until recently, the use of electronic features like the ones above has been limited to durable injection devices, as the additional cost connected with an inclusion of such features in a disposable injection device has been considered to lead to an economically unviable end product. However, the advances within particularly printed electronics are promising vis-à-vis the possibility of producing disposable injection devices with integrated electronic components at a reasonable cost.

WO 2015/071354 A1 (Novo Nordisk A/S) discloses a drug delivery device having a flexible sheet mounted at least in part to the exterior of its housing, the flexible sheet carrying e.g. printed electronic components such as a display, a processor, an energy source, and input means actuatable by a an action performed on or by the device. The display is configured to visually indicate e.g. the size of a set dose, the size of an expelled dose, and/or a time parameter in response to actuation of the input means. The input means are exemplified by various switch structures, each adapted to provide connection to an interior device component through an opening in the housing.

Switch structures are generally prone to errors, for example faulty switch activations, during handling or transportation. In particular, in case of the device being unintentionally dropped on a hard surface, an impact may cause erroneous switch activation.

SUMMARY OF THE INVENTION

It is an object of the invention to eliminate or reduce at least one drawback of the prior art, or to provide a useful alternative to prior art solutions.

In particular, it is an object of the invention to provide a drug injection device having means for reliably enabling detection of a change of state of the drug injection device. It is a further object of the invention to provide an improved drug injection device having means for electronic determination of a set and/or expelled dose of drug. It is an even further object of the invention to provide such a drug injection device which is relatively simple and which enables inexpensive manufacturing.

In the disclosure of the present invention, aspects and embodiments will be described which will address one or more of the above objects and/or which will address objects apparent from the following text.

A first aspect of the present invention relates to a drug injection device for expelling a dose of drug from a held drug container, the drug injection device comprising:
  a first element and a second element configured to undergo movement relative to each other, said movement being a unidirectional movement in a first direction corresponding to a predetermined action performed on or by the drug injection device and representing an amount of drug delivered or to be delivered from the drug injection device, wherein the first element comprises a protrusion configuration comprising a plurality of serially disposed protrusions equally spaced along the first direction of movement, wherein the second element comprises first and second deflectable transducers, each of the first and the second deflectable transducer being configured for sequentially cooperating with the plurality of protrusions of the first element to become deflected thereby generating an activation signal as the deflectable transducer is deflected when travelling past each protrusion, and a processor electrically connected with the first and second deflectable transducers to register generated activation signals from the first and second deflectable transducers, and being configured to determine, from registered activation signals, an amount of drug delivered or to be delivered from the drug injection device, wherein the protrusion configuration is so disposed on the first element and the first and second deflectable transducers are so disposed on the second element so that a second activation signal generated by the second deflectable transducer is delayed relative to a first activation signal generated by the first deflectable transducer as the first element and the second element move relative to each other, wherein the processor is configured to register the first activation signal and the second activation signal and to determine a time delay there between, and wherein the processor is configured to provide a) a first control action if said time delay is above or equal to a pre-defined value, and b) a second control action if said time delay is below said pre-defined value.

In accordance with such device, if the time delay determined by the processor indicates that a proper sequence between the first and second activation signals has occurred, i.e. a sequence which is representative for said predetermined action, this will be used to register said predetermined action performed on or by the drug injection device and representing an amount of drug delivered or to be delivered from the drug injection device. In accordance herewith, the first control action is provided by the processor.

In accordance with said first aspect of the invention, for the correctly working device, by utilizing the specific sequence of the first and second activation signals, the manufacturer of the drug injection device may specify a range of time delays between the first activation signal and the second activation signal, i.e. a range of time delays, including the pre-defined value, likely to occur when operating a perfectly functioning device which is operated in the intended manner, such as during expelling of a dose of drug. In accordance herewith, for the particular drug injection device in question, for experienced time delay values lower than the said range of time delays, such lower time delays are not likely to occur during expelling of a dose from a perfectly functioning device, and which is operated in the intended way. Hence the specific sequence of the first and second activation signals is used to error mitigate the encoder, i.e. the first and second deflectable transducers, for false triggers and/or malfunctioning of the encoder.

If the time delay registered by the processor is below the pre-defined value, e.g. signifying an incorrect condition, the second control action may be used to provide an indication of the incorrect condition, acknowledging that the second control action differs from the first control action. For example, such incorrect condition may occur if the device is being unintentionally dropped on a hard surface, which may cause an uncontrolled activation of the first and second deflectable transducers, typically causing a pair of signals generated by the first and second deflectable transducers to be provided simultaneously, or having a time delay between the two activation signals below the pre-defined value. Hence, the processor may be configured to provide the second control action. Such control action may e.g. provide an action which filters out erroneous signals from the first and second deflectable transducers so that these are not used for registering said predetermined action, performed on or by the drug injection device, and representing an amount of drug delivered or to be delivered from the drug injection device.

The same configuration with two individual deflectable transducers may be used to detect if one of the two deflectable transducers is faulty, or totally defective, i.e. not generating any activation signals at all. If this should occur, the proper pre-defined sequence of activation signals from the first and the second deflectable transducers will not be met, and an error condition may be determined and flagged.

Another event which may arise, such as an ESD pulse hitting one or both arms, will not have the correct sequence of activation signals as compared with the sequence which is generated in response to the predetermined action. By using the solution according to the first aspect, potential ESD pulses can be determined as a faulty condition and the second control action is carried out.

Errors can furthermore be detected if one of the activation signals from the deflectable transducers is not being received by the processor due to one or more of the following conditions: a) a failing sensor, b) a broken line between sensor and processor input, or c) an input pin on the processor having lost contact to the electronic circuitry.

The drug injection device may in some embodiments comprise an energy source being coupled to the processor for providing power to process signals recorded by the first and second deflectable transducers. Such energy source may comprise a battery such as a printed battery or a coin cell battery. Alternatively, or in addition, the drug injection device may include circuitry which is configured for harvesting energy from an energy field provided by an external device.

The drug injection device may further comprise an electronic memory unit adapted to store information pertaining to a drug expelling action, and/or to a dose setting action, such as e.g. the time of the drug expelling action and/or the size of the dose expelled from the reservoir in the course of the drug expelling action. The electronic memory unit, together with other electronic components of the drug injection device, may be formed, such as by being printed, or mounted on a carrier. The carrier may take the form of a substrate, or may take the form of a flexible sheet.

The deflectable transducers, the processor and/or the energy source may be arranged on a single, flexible sheet which is mounted, at least in part, on or in the housing. The arrangement of the electronic components on a flexible sheet allows for faster and cheaper mass production in that multiple sheets may be prepared in a continuous process, e.g. by roll-to-roll printing.

Further electronic components may be comprised by the drug injection device and be coupled to the processor, such as e.g. an antenna for wirelessly relaying data to an external receiver. Also, in addition or as a supplement, an electronically controlled display may be coupled to the processor for displaying information related to data correlated to one or more first control actions and/or one or more second control actions. All such additional electronic components may be arranged on said single, flexible sheet.

In some variants, the drug injection device does not include an electronically controlled display. In such variants, the drug injection device includes a communication unit and an antenna for wirelessly relaying data to an external receiver. In particular variants thereof, the drug injection device may include a dose setting mechanism and a mechanically operated dose dial display which is utilized for visually indicating a set dose to be expelled from the injection device, but wherein the antenna and the communication unit is utilized for relaying data indicative of one or more expelled dosage amounts from the drug injection device to an external receiving device.

In some embodiments, each of the first and second deflectable transducers comprises a deflectable portion arranged to become deflected in a direction generally transverse to the first direction by cooperating with the protrusions of the protrusion configuration.

In some forms, each of the first and the second deflectable transducer is disposed on a respective deflectable arm defined by a resiliently deflectable polymeric or metallic material portion configured to become deflected in a direction generally transverse to the first direction upon cooperating with the protrusions of the protrusion configuration.

Engaging geometries of the protrusions of the protrusion configuration and the deflectable arm of the first and/or the second deflectable transducers may in some embodiments define a click mechanism that generates audible clicks as the protrusions pass the deflectable arm. Hence, the registering of said predetermined action performed on or by the drug injection device and representing an amount of drug delivered or to be delivered from the drug injection device will be synchronized with the audible clicks that the user hears and registers during use of the device.

In some embodiments, for each of the first and/or the second deflectable transducer, engaging geometries of the protrusions of the protrusion configuration and the respective deflectable arm of the first and the second deflectable transducer is configured to provide a gradually rising deflection of the deflectable arm into a biased state followed by an abrupt release from the biased state as each protrusion pass the deflectable arm.

The drug injection device may in certain embodiments define a ratchet mechanism between the first element and the second element so as to prevent relative movement between the first element and the second element in a direction opposite to said first direction and to allow movement in the first direction.

In some embodiments, the first element and the second element are arranged co-axially along a central axis, the first element and/or the second element being rotationally movable around the central axis for relative rotational movement in a first rotational direction.

The first element may be formed so that it defines a circular element having the plurality of protrusions evenly arranged in the angular direction and wherein the plurality of protrusions are arranged to protrude radially to radially deflect the first and the second deflectable transducers. The protrusions may either protrude radially outwards or radially inwards. In some embodiments the first deflectable transducer cooperates with radially outwards protruding protrusions whereas the second deflectable transducer cooperates with radially inwards protruding protrusions. In still other embodiments, one or both of the first and/or the second deflectable transducers disposed on the second element are arranged to deflect axially when cooperating with axially protruding protrusions disposed on the first element.

In some embodiments, the first and the second deflectable transducers are disposed in a generally symmetrical configuration around the central axis.

In particular embodiments of the drug injection device the serially disposed protrusions of the first element are equally spaced with distance S. The first and second deflectable transducers are positioned on the second element so that an activation signal from the second deflectable transducer and an activation signal from the first deflectable transducer are generated within a relative movement between the first element and the second element corresponding to less than 0.5 times S, more preferably less than 0.4 times S, more preferably less than 0.3 times S, and most preferably less than 0.2 times S.

In some embodiments, the processor comprises a counter wherein the processor is configured to modify a value of the counter upon performing the first control action, and configured not to modify the value of the counter upon performing the second control action. In some embodiments, the processor is configured for storing the value of the counter representing the number of first control actions for later retrieval. Also, in further embodiments, the processor is configured for storing one or more second control actions for later retrieval.

In some embodiments, the processor stores one or more sets of data, wherein each set of data comprises the value of the counter and the associated time value, wherein each set of data represents an expelled dosage amount and the associated time of expelling.

In other embodiments, the processor stores, upon performing said first control action, a time value representing said predetermined action performed and registered, so that each first control action and the associated time value is stored by the processor. The processor may be configured not to store, upon performing said second control action, any time values. Alternatively, upon performing said second control action, a time value is stored together with a flag indicating an error condition.

In different embodiments, the first and/or the second deflectable transducers are provided as, or comprises, one or more of a piezoelectric sensor, a strain gauge, a galvanic foil sensor, and a capacitive sensor having an elastic dielectric between two electrodes.

In some embodiments the first and/or the second deflectable transducers comprise a printed piezoelectric material.

The first and the second deflectable transducers, and the processor may be arranged on a flexible sheet. The flexible sheet may further include an antenna and a wireless communication unit. Also, the flexible sheet may in some embodiments comprise an energy source such as one or more printed batteries. In some forms, the drug injection device does not include an electronically controlled display. In other forms, the drug injection device includes an electronically controlled display.

In particular forms the drug injection device defines a housing extending along a longitudinal axis, and further comprises a drug expelling mechanism for expelling a volume of drug from a reservoir, wherein the first element and/or the second element form part of the drug expelling mechanism, and wherein a relative unidirectional movement between the first element and the second element about the longitudinal axis is provided during a drug expelling action in accordance with an expelled dose.

In some embodiments, the drug expelling mechanism is configured as a spring drive mechanism wherein energy stored in a tensed spring is utilized for expelling a dose of drug from the injection device. In other embodiments, the drug expelling mechanism is a fully manual type, wherein the force needed for driving the expelling of a dose of drug from the drug injection device is exerted by a user's hand. Both the embodiment comprising a spring-drive expelling mechanism, as well as the fully manual type expelling mechanism, a maximum expelling speed is typically predictable, and the sequence between the first activation signal and the second activation signal, e.g. the time delay between these signals, is likewise predictable. Hence, this provides optimal conditions for providing the proposed error mitigation in accordance with the first aspect of the invention.

In further embodiments thereof, the drug injection device further comprises a dose setting mechanism operable to set a dose of drug to be expelled from the held drug container by the drug expelling mechanism. In certain embodiments that includes a dose setting mechanism, the first element and/or the second element form part of the dose setting mechanism, and wherein a relative unidirectional movement between the first element and the second element about the longitudinal axis is provided during a dose setting action.

In still other embodiments that includes a dose setting mechanism, said relative unidirectional movement between the first element and the second element about the longitudinal axis is provided during a drug expelling action in accordance with an expelled dose, but wherein said relative unidirectional movement is not performed during dose setting, i.e. during dialling up a dose or dialling down an initially set dose.

In some embodiments, the drug injection device defines a disposable injection device for expelling one or more doses of drug from a prefilled and non-exchangeable drug container, such as a piston equipped cartridge or syringe. In other embodiments, the drug injection device defines a durable injection device for expelling one or more doses of drug from a pre-filled and exchangeable drug container or syringe.

As used herein the term "drug injection device" covers all types of devices for administering drug transcutaneously, i.e. including devices which are conventionally labelled injection devices (with or without an injection needle), where the drug is delivered over a relatively short time span, and devices which are conventionally labelled infusion devices, where the drug is delivered continuously over a longer period of time.

Also, as used herein, the terms "distal" and "proximal" denote positions at or directions along a drug injection device, where "distal" refers to the drug outlet end and "proximal" refers to the end opposite the drug outlet end.

In the present specification, reference to a certain aspect or a certain embodiment (e.g. "an aspect", "a first aspect", "one embodiment", "an exemplary embodiment", or the like) signifies that a particular feature, structure, or characteristic described in connection with the respective aspect or embodiment is included in, or inherent of, at least that one aspect or embodiment of the invention, but not necessarily in/of all aspects or embodiments of the invention. It is emphasized, however, that any combination of the various features, structures and/or characteristics described in relation to the invention is encompassed by the invention unless expressly stated herein or clearly contradicted by context.

The use of any and all examples, or exemplary language (e.g., such as, etc.), in the text is intended to merely illuminate the invention and does not pose a limitation on the scope of the same, unless otherwise claimed. Further, no language or wording in the specification should be construed as indicating any non-claimed element as essential to the practice of the invention.

BRIEF DESCRIPTION OF THE DRAWINGS

In the following the invention will be further described with references to the drawings, wherein.

In the figures like structures are mainly identified by like reference numerals.

DESCRIPTION OF EXEMPLARY EMBODIMENTS

When in the following relative expressions, such as "clockwise" and "counter-clockwise", "left" and "right", etc. are used, these refer to the appended figures and not necessarily to an actual situation of use. The shown figures are schematic representations for which reason the configuration of the different structures as well as their relative dimensions are intended to serve illustrative purposes only.

Figure 1:
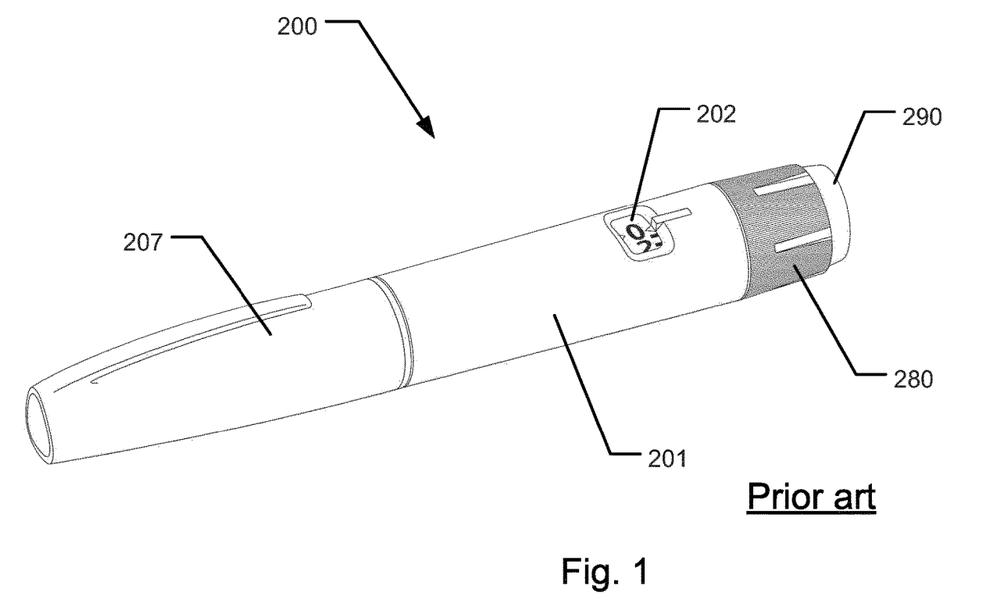
FIG. 1 shows a perspective view of a prior art pen device 200.
Figure 2:
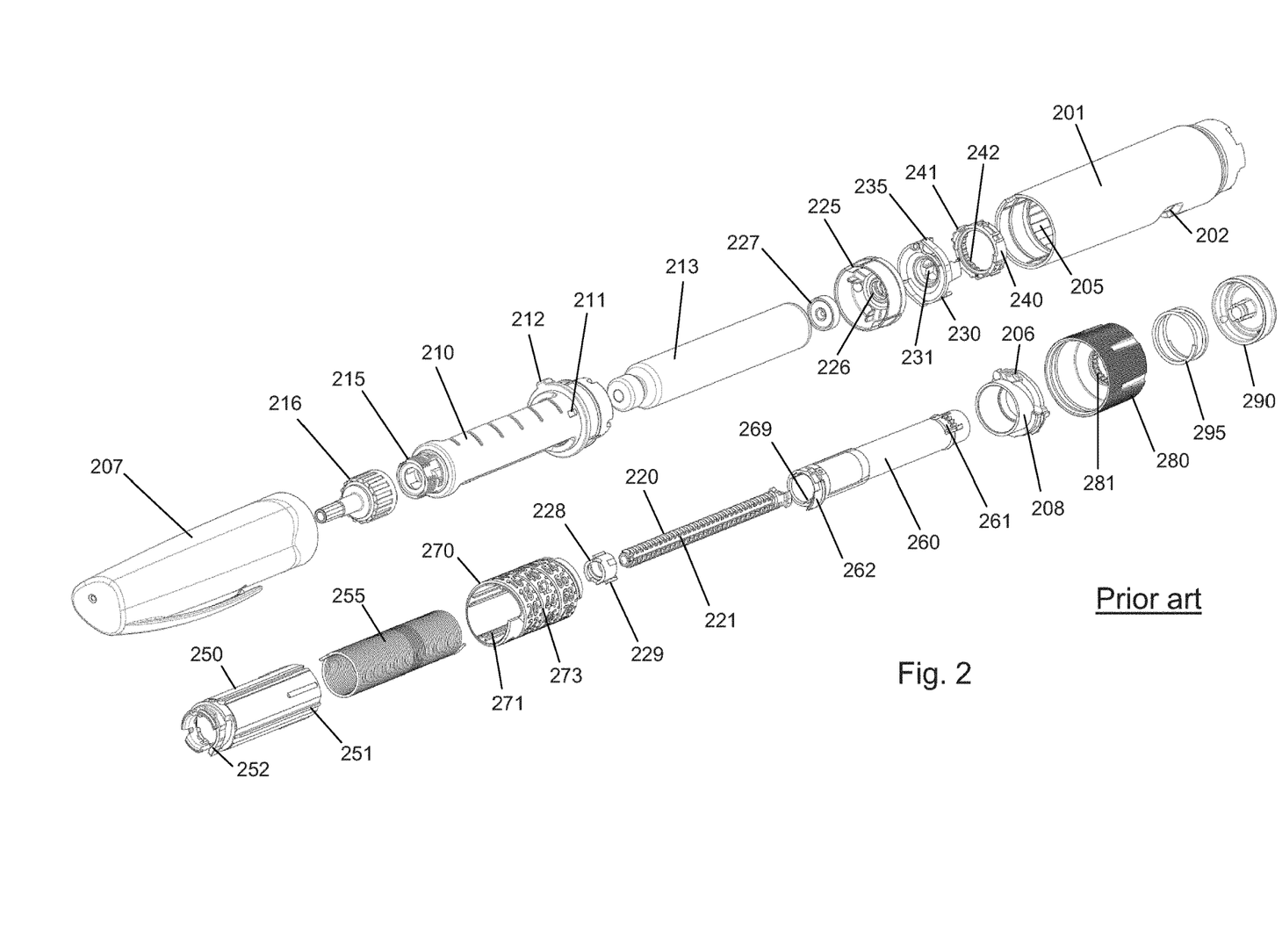
FIG. 2 shows in an exploded view the components of the pen device of FIG. 1, FIGS. 3A and 3B show in sectional views an expelling mechanism of the pen device of FIG. 1 in two states.
Figure 3A:
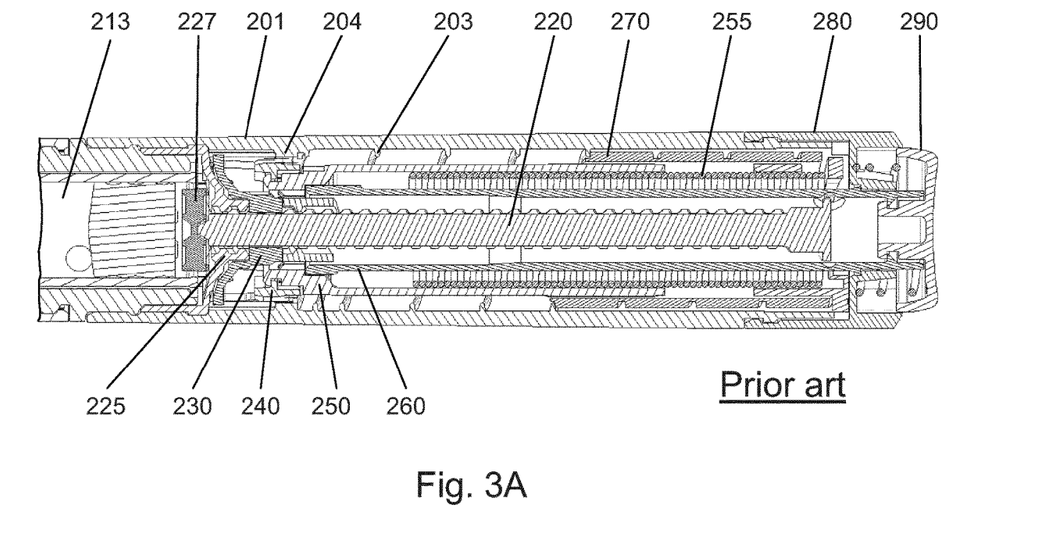
Figure 3B:
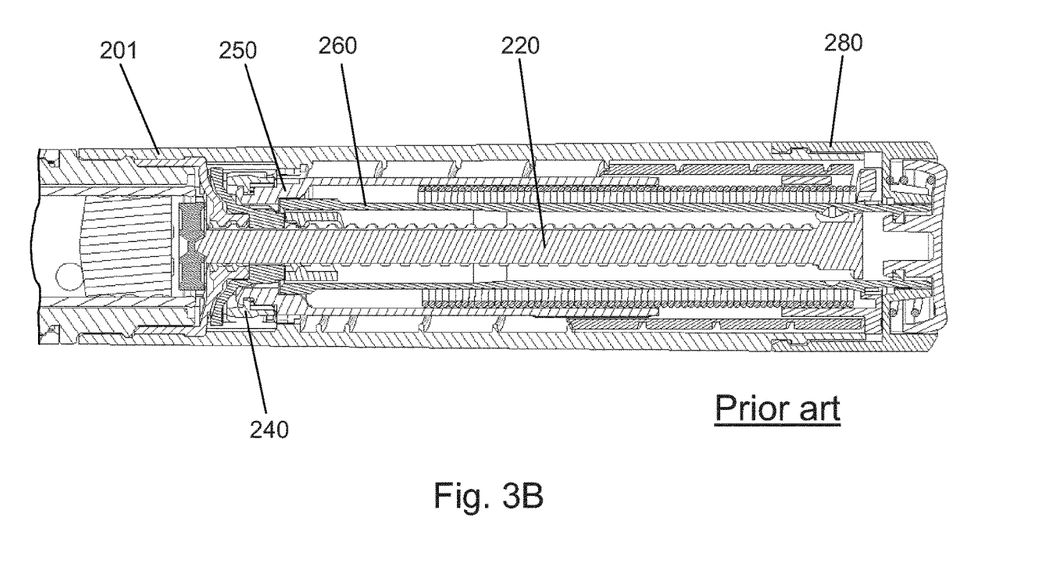

FIG. 1 shows a prior art drug delivery device in the form of a pen-formed auto-injection device 200, i.e. a so-called "injection pen" that includes an expelling mechanism incorporating a spring drive. FIG. 2 shows an exploded view of the prior art auto-injection device 200 shown in FIG. 1. FIGS. 3A and 3B show cross sectional views of the expelling mechanism of the prior art auto-injection device 200 shown in FIGS. 1 and 2 where FIG. 3A shows the device in dose setting state and FIG. 3B shows the device in dose expelling state.

In the present context the device 200 represents a "generic" drug delivery device providing a specific example of a device which, in accordance with the present invention, may be modified in order to obtain a device that provides electronic monitoring of movements within the drug delivery.

The pen device 200 comprises a cap part 207 and a main part having a proximal body or drive assembly portion with a housing 201 in which a drug expelling mechanism is arranged or integrated, and a distal cartridge holder portion in which a drug-filled transparent cartridge 213 with a distal needle-penetrable septum is arranged and retained in place by a non-removable cartridge holder attached to the proximal portion, the cartridge holder having openings allowing a portion of the cartridge to be inspected as well as distal coupling means 215 allowing a needle assembly to be releasably mounted. The cartridge is provided with a piston driven by a piston rod forming part of the expelling mechanism and may for example contain an insulin, GLP-1 or growth hormone formulation. A proximal-most rotatable dose dial member 280 serves to manually set a desired dose of drug shown in display window 202 and which can then be expelled when the release button 290 is actuated. Depending on the type of expelling mechanism embodied in the drug delivery device, the expelling mechanism may comprise a spring as in the shown embodiment which is strained during dose setting and then released to drive the piston rod when the release button 290 is actuated.

As appears, FIG. 1 shows a drug delivery device of the pre-filled type, i.e. it is supplied with a pre-mounted cartridge and is to be discarded when the cartridge has been emptied. In alternative embodiments, and in accordance with the present invention, the drug delivery device may be designed to allow a loaded cartridge to be replaced, e.g. in the form of a "rear-loaded" drug delivery device in which the cartridge holder is adapted to be removed from the device main portion, or alternatively in the form of a "front-loaded" device in which a cartridge is inserted through a distal opening in the cartridge holder which is non-removable attached to the main part of the device.

More specifically, referring to FIG. 2, the pen comprises a tubular housing 201 with a window opening 202 and onto which a cartridge holder 210 is fixedly mounted, a drug-filled cartridge 213 being arranged in the cartridge holder. The cartridge holder is provided with distal coupling means 215 allowing a needle assembly 216 to be releasably mounted, proximal coupling means in the form of two opposed protrusions 211 allowing a cap 207 to be releasably mounted covering the cartridge holder and a mounted needle assembly, as well as a protrusion 212 preventing the pen from rolling on e.g. a table top. In the housing distal end a nut element 225 is fixedly mounted, the nut element comprising a central threaded bore 226, and in the housing proximal end a spring base member 208 with a central opening is fixedly mounted. A drive system comprises a threaded piston rod 220 having two opposed longitudinal grooves and being received in the nut element threaded bore, a ring-formed piston rod drive element 230 rotationally arranged in the housing, and a ring-formed clutch element 240 which is in rotational engagement with the drive element (see below), the engagement allowing axial movement of the clutch element. The clutch element is provided with outer spline elements 241 adapted to engage corresponding splines on the housing inner surface, this allowing the clutch element to be moved between a rotationally locked proximal position, in which the splines are in engagement, and a rotationally free distal position in which the splines are out of engagement. As just mentioned, in both positions the clutch element 240 is rotationally locked to the drive element 230. The drive element comprises a central bore with two opposed protrusions 231 in engagement with the grooves on the piston rod whereby rotation of the drive element results in rotation and thereby distal axial movement of the piston rod due to the threaded engagement between the piston rod and the nut element. The drive element further comprises a pair of opposed circumferentially extending flexible ratchet arms 235 adapted to engage corresponding ratchet teeth 205 arranged on the housing inner surface. The drive element and the clutch element comprise cooperating coupling structures rotationally locking them together but allowing the clutch element to be moved axially, this allowing the clutch element to be moved axially to its distal position in which it is allowed to rotate, thereby transmitting rotational movement from the dial system (see below) to the drive system. The interaction between the clutch element, the drive element and the housing will be shown and described in greater detail with reference to FIGS. 3C and 3D.

On the piston rod an end-of-content (EOC) member 228 (EOC limiter) is threadedly mounted and on the distal end a washer 227 is rotationally mounted. The EOC member comprises a pair of opposed radial projections 229 for engagement with the reset tube (see below).

The dial system comprises a ratchet tube 250, a reset tube 260, a scale drum 270 with an outer helically arranged row of dose numerals, a user-operated dose dial member 280 for setting a dose of drug to be expelled, a release button 290 and a torque spring 255 (see FIGS. 3A and 3B). The reset tube is mounted axially locked inside the ratchet tube but is allowed to rotate a few degrees (see below). The reset tube comprises on its inner surface two opposed longitudinal grooves 269 adapted to engage the radial projections 229 of the EOC member, whereby the EOC can be rotated by the reset tube but is allowed to move axially. The clutch element is mounted axially locked on the outer distal end portion of the ratchet tube 250, this providing that the ratchet tube can be moved axially in and out of rotational engagement with the housing via the clutch element. The dose dial member 280 is mounted axially locked but rotationally free on the housing proximal end, the dose dial member being under normal operation rotationally locked to the reset tube (see below), whereby rotation of dose dial member results in a corresponding rotation of the reset tube and thereby the ratchet tube. The release button 290 is axially locked to the reset tube but is free to rotate. A return spring 295 provides a proximally directed force on the button and the thereto mounted reset tube. The scale drum 270 is arranged in the circumferential space between the ratchet tube and the housing, the drum being rotationally locked to the ratchet tube via cooperating longitudinal splines 251, 271 and being in rotational threaded engagement with the inner surface of the housing via cooperating thread structures 203, 273, whereby the row of numerals passes the window opening 202 in the housing when the drum is rotated relative to the housing by the ratchet tube. The torque spring is arranged in the circumferential space between the ratchet tube and the reset tube and is at its proximal end secured to the spring base member 208 and at its distal end to the ratchet tube, whereby the spring is strained when the ratchet tube is rotated relative to the housing by rotation of the dial member. A ratchet mechanism with a flexible ratchet arm 252 is provided between the ratchet tube and the clutch element, the latter being provided with an inner circumferential teeth structures 242, each tooth providing a ratchet stop such that the ratchet tube is held in the position to which it is rotated by a user via the reset tube when a dose is set. In order to allow a set dose to be reduced a ratchet release mechanism 262 is provided on the reset tube and acting on the ratchet tube, this allowing a set dose to be reduced by one or more ratchet increments by turning the dial member in the opposite direction, the release mechanism being actuated when the reset tube is rotated the above-described few degrees relative to the ratchet tube.

Having described the different components of the expelling mechanism and their functional relationship, operation of the mechanism will be described next with reference mainly to FIGS. 3A and 3B.

The pen mechanism can be considered as two interacting systems, a dose system and a dial system, this as described above. During dose setting the dial mechanism rotates and a torsion spring of the spring drive is loaded. The dose mechanism is locked to the housing and cannot move. When the push button is pushed down, the dose mechanism is released from the housing and due to the engagement to the dial system, the torsion spring will now rotate back the dial system to the starting point and rotate the dose system along with it.

The central part of the dose mechanism is the piston rod 220, the actual displacement of the piston being performed by the piston rod. During dose delivery, the piston rod is rotated by the drive element 230 and due to the threaded interaction with the nut element 225 which is fixed to the housing, the piston rod moves forward in the distal direction. Between the rubber piston and the piston rod, the piston washer 227 is placed which serves as an axial bearing for the rotating piston rod and evens out the pressure on the rubber piston. As the piston rod has a non-circular cross section where the piston rod drive element engages with the piston rod, the drive element is locked rotationally to the piston rod, but free to move along the piston rod axis. Consequently, rotation of the drive element results in a linear forwards movement of the piston. The drive element is provided with small ratchet arms 234 which prevent the drive element from rotating clockwise (seen from the push button end). Due to the engagement with the drive element, the piston rod can thus only move forwards. During dose delivery, the drive element rotates anti-clockwise and the ratchet arms 235 provide the user with small clicks due to the engagement with the ratchet teeth 205, e.g. one click per unit of insulin expelled.

Turning to the dial system, the dose is set and reset by turning the dose dial member 280. When turning the dial, the reset tube 260, the EOC member 228, the ratchet tube 250 and the scale drum 270 all turn with it. As the ratchet tube is connected to the distal end of the torque spring 255, the spring is loaded. During dose setting, the arm 252 of the ratchet performs a dial click for each unit dialed due to the interaction with the inner teeth structure 242 of the clutch element. In the shown embodiment the clutch element is provided with 24 ratchet stops providing 24 clicks (increments) for a full 360 degrees rotation relative to the housing. The spring is preloaded during assembly which enables the mechanism to deliver both small and large doses within an acceptable speed interval. As the scale drum is rotationally engaged with the ratchet tube, but movable in the axial direction and the scale drum is in threaded engagement with the housing, the scale drum will move in a helical pattern when the dial system is turned, the number corresponding to the set dose being shown in the housing window 202.

The ratchet 252, 242 between the ratchet tube and the clutch element 240 prevents the spring from turning back the parts. During resetting, the reset tube moves the ratchet arm 252, thereby releasing the ratchet click by click, one click corresponding to one unit IU of insulin in the described embodiment. More specifically, when the dial member is turned clockwise, the reset tube simply rotates the ratchet tube allowing the arm of the ratchet to freely interact with the teeth structures 242 in the clutch element. When the dial member is turned counter-clockwise, the reset tube interacts directly with the ratchet click arm forcing the click arm towards the centre of the pen away from the teeth in the clutch, thus allowing the click arm on the ratchet to move "one click" backwards due to torque caused by the loaded spring.

To deliver a set dose, the release button 290 is pushed in the distal direction by the user as shown in FIG. 3B. The reset tube 260 decouples from the dial member and subsequently the clutch element 240 disengages the housing splines 204. Now the dial mechanism returns to "zero" together with the drive element 230, this leading to a dose of drug being expelled. It is possible to stop and start a dose at any time by releasing or pushing the push button at any time during drug delivery. A dose of less than 5 IU normally cannot be paused, since the rubber piston is compressed very quickly leading to a compression of the rubber piston and subsequently delivery of insulin when the piston returns to the original dimensions.

The EOC feature prevents the user from setting a larger dose than left in the cartridge. The EOC member 228 is rotationally locked to the reset tube, which makes the EOC member rotate during dose setting, resetting and dose delivery, during which it can be moved axially back and forth following the thread of the piston rod. When it reaches the proximal end of the piston rod a stop is provided, this preventing all the connected parts, including the dial member, from being rotated further in the dose setting direction, i.e. the now set dose corresponds to the remaining drug content in the cartridge.

The scale drum 270 is provided with a distal stop surface adapted to engage a corresponding stop surface on the housing inner surface, this providing a maximum dose stop for the scale drum preventing all the connected parts, including the dial member, from being rotated further in the dose setting direction. In the shown embodiment the maximum dose is set to 80 IU. Correspondingly, the scale drum is provided with a proximal stop surface adapted to engage a corresponding stop surface on the spring base member, this preventing all the connected parts, including the dial member, from being rotated further in the dose expelling direction, thereby providing a "zero" stop for the entire expelling mechanism. In the following, the position that the dial member assumes after completion of the expelling of a set dose will be referred to as the "zero dose position".

To prevent accidental over-dosage in case something should fail in the dialing mechanism allowing the scale drum to move beyond its zero-position, the EOC member serves to provide a security system. More specifically, in an initial state with a full cartridge the EOC member is positioned in a distal-most axial position in contact with the drive element. After a given dose has been expelled the EOC member will again be positioned in contact with the drive element. Correspondingly, the EOC member will lock against the drive element in case the mechanism tries to deliver a dose beyond the zero-position. Due to tolerances and flexibility of the different parts of the mechanism the EOC will travel a short distance allowing a small "over dose" of drug to be expelled, e.g. 3-5 IU of insulin.

The expelling mechanism further comprises an end-of-dose (EOD) click feature providing a distinct feedback at the end of an expelled dose informing the user that the full amount of drug has been expelled. More specifically, the EOD function is made by the interaction between the spring base and the scale drum. When the scale drum returns to zero, a small click arm 206 on the spring base is forced backwards by the progressing scale drum. Just before "zero" the arm is released and the arm hits a countersunk surface on the scale drum.

The shown mechanism is further provided with a torque limiter in order to protect the mechanism from overload applied by the user via the dose dial member. This feature is provided by the interface between the dose dial member and the reset tube which as described above are rotationally locked to each other. More specifically, the dose dial member is provided with a circumferential inner teeth structure 281 engaging a number of corresponding teeth arranged on a flexible carrier portion 261 of the reset tube. The reset tube teeth are designed to transmit a torque of a given specified maximum size, e.g. 150-300 Nmm, above which the flexible carrier portion and the teeth will bend inwards and make the dose dial member turn without rotating the rest of the dial mechanism. Thus, the mechanism inside the pen cannot be stressed at a higher load than the torque limiter transmits through the teeth.

Figure 3C:
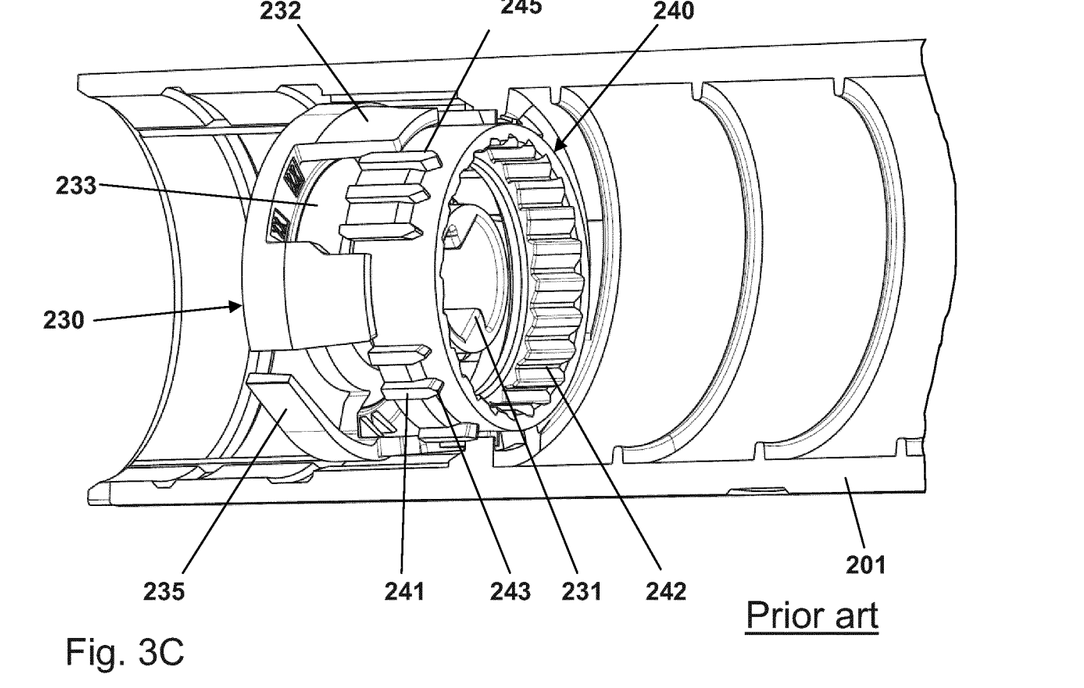
FIGS. 3C-3E show components of the pen device of FIG. 1.
Figure 3D:
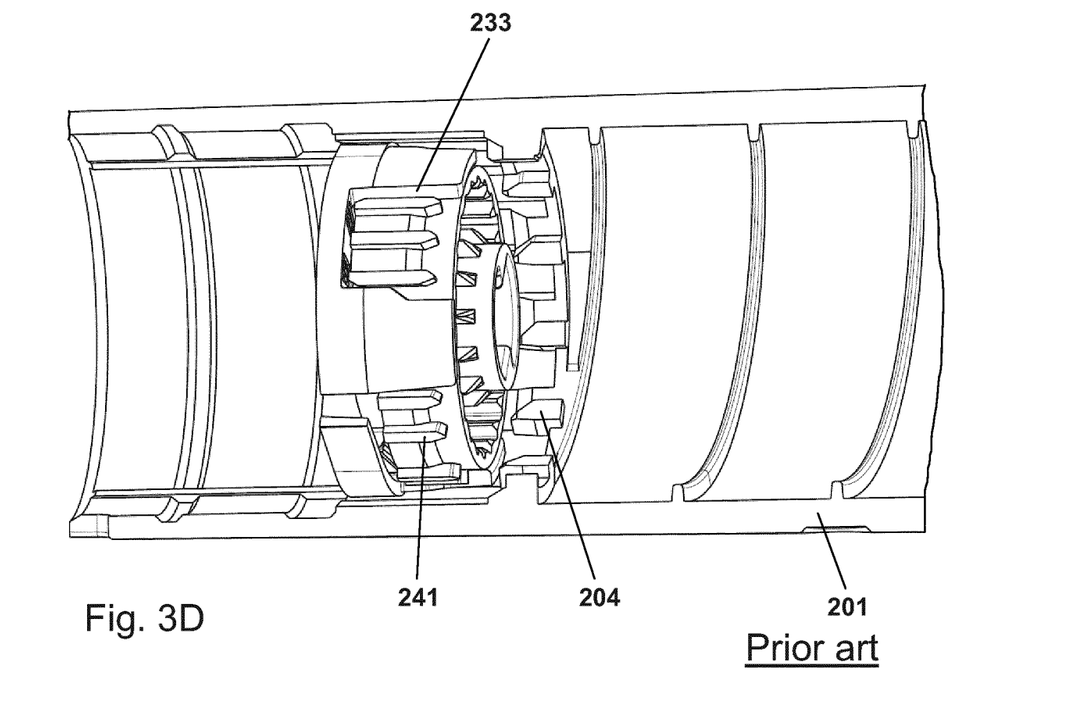
Figure 3E:
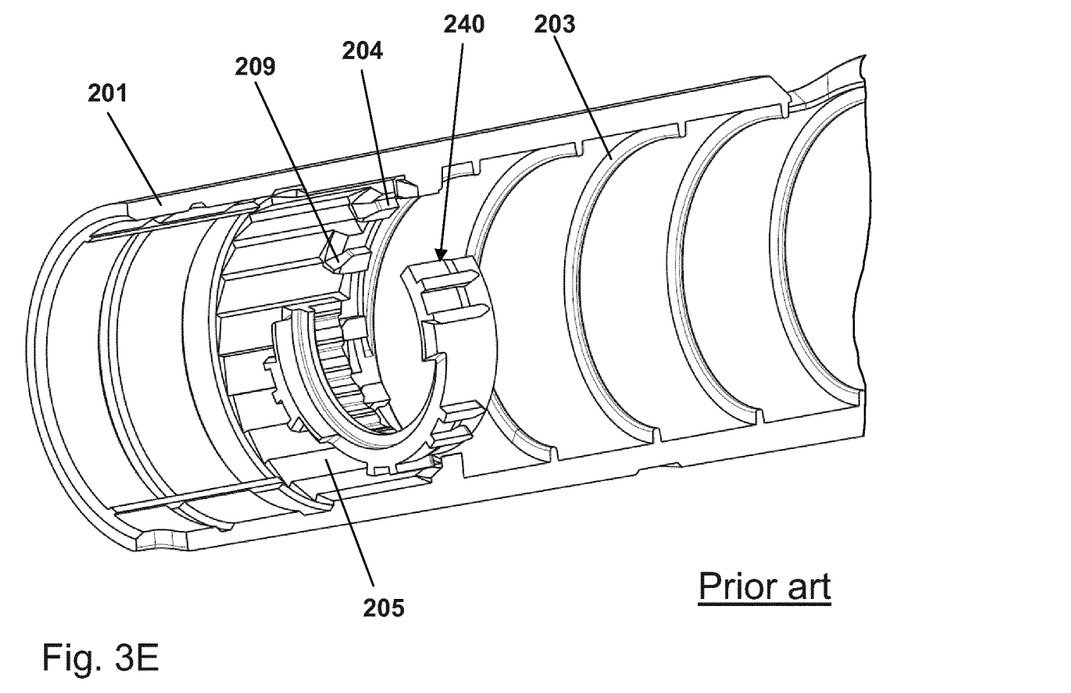

In FIG. 3C the clutch element, the drive element and the housing (in partial) are shown in the dose setting state, and in FIG. 3D the same components are shown in the expelling state. As appears, the piston rod on which the drive element is arranged and the ratchet tube on which the clutch element is mounted are not shown. To better show the structures provided on the inner surface of the housing FIG. 3E shows a partial clutch element 240 arranged in the housing 201.

The inner surface of the housing 201 comprises a circumferential ring-formed array of axially oriented spline elements 204 protruding into the interior, each having a pointed distal end 209, as well as a circumferential ring-formed array of one-way ratchet teeth 205. The inner surface further comprises a male helical thread 203 adapted to engage the female helical thread 273 on the scale drum 270. A distal circumferential groove is formed to engage and mount the nut element 225. The clutch element 240 comprises an inner circumferential ring-formed array of ratchet teeth 242 adapted to engage the ratchet arm 252 on the ratchet tube 250, and an outer circumferential ring-formed array of axially oriented spline elements 241 adapted to engage the spline elements 204 of the housing as well as the coupling slots in the drive element (see below), each spline having a pointed proximal end 243. The drive element 230 comprises a pair of opposed coupling portions each comprising two proximally extending skirt portions 232 between which an axially extending coupling slot 233 is formed, the slot being adapted to engage a portion of the clutch element spline elements. In this way the engaging surfaces serve to transmit a rotational force and thereby torque from the clutch element to the drive element in the expelling state. The drive element further comprises a pair of opposed circumferentially extending flexible ratchet arms adapted to engage the ring-formed array of one-way ratchet teeth 205. During dose delivery, the drive element rotates anti-clockwise and the ratchet arms 235 also provide the user with small clicks due to the engagement with the ratchet teeth 205, e.g. one click per unit of insulin expelled. In the shown embodiment 24 ratchet teeth are provided corresponding to 15 degrees rotation per unit of insulin. The central bore of the drive element comprises two opposed protrusions 231 adapted to engage with the axially oriented grooves on the piston rod.

In the dose setting state shown in FIG. 3C the spline elements 241 of the clutch element are in engagement with the spline elements 204 of the housing thereby rotationally locking the clutch element relative to the housing. As can be seen from FIG. 3C a group of clutch spline elements are received in the corresponding coupling slot with a slight rotational play. In the expelling state shown in FIG. 3D the spline elements 241 of the clutch element are moved distally out of engagement with the spline elements 204 of the housing thereby allowing rotation of the clutch element relative to the housing. As can be seen from FIG. 3D the group of clutch spline elements are now received in the corresponding coupling slot without rotational play.

FIG. 3C shows the clutch element 240 showing the above-described inner circumferential ring-formed array of ratchet teeth 242 and the outer circumferential ring-formed array of axially oriented spline elements 241. As appears, the spline elements are not arranged equidistantly on the ring but in groups, the groups comprising two opposed coupling groups 245 serving as the coupling means engaging the coupling slots 233. Whereas thus only some of the spline elements serve as coupling means between the clutch element and the drive element they all serve as coupling means between the clutch element and the housing splines 204.

Figure 4:
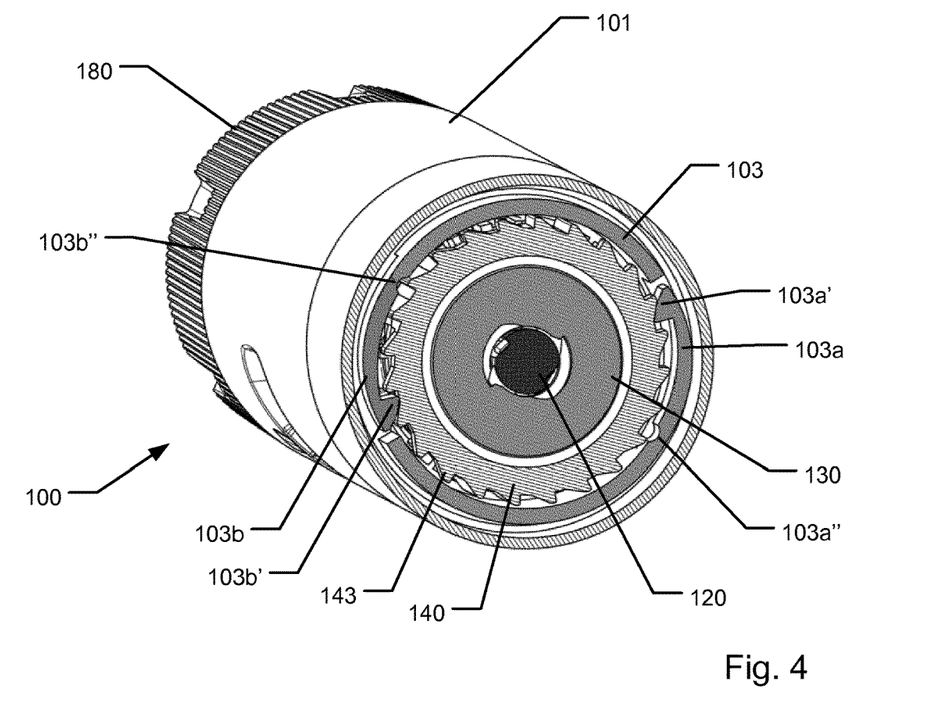
FIG. 4 is a perspective cross sectional view of a pen device 100 of a first embodiment according to the invention with the pen device with first and second deflectable transducers in a first state.
Figure 5:
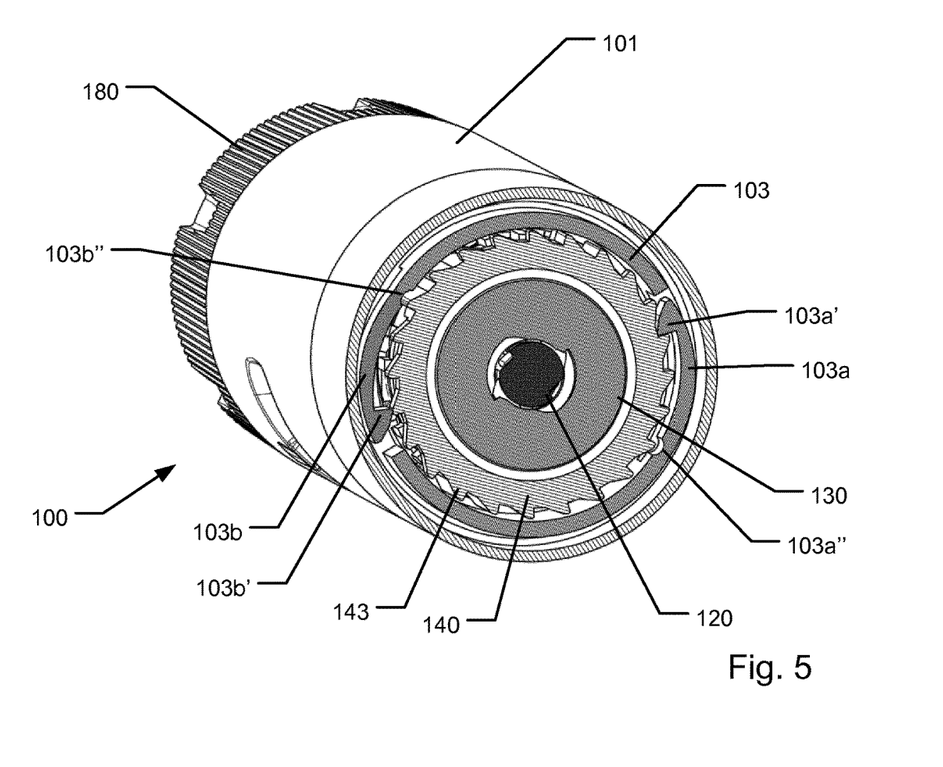
FIG. 5 is a similar view with the pen device 100 with the first and second deflectable transducers in a second state, FIG. 6 schematically depicts sensor signals received from the first and second deflectable transducer during operation.

Each of FIGS. 4 and 5 depicts a cross sectional view of a pen injection device 100 according to a first exemplary embodiment of the invention, with the two views depicting the same cross section but in two consecutive states. Similarly to the prior art pen injection device 200 described above, as best viewed in FIG. 8, the pen injection device 100 comprises a tubular housing 101, a proximal-most rotatable dose dial member 180, a push-button 190, and an injection needle 116 attached at the distal end of the device. FIGS. 4 and 5 further show a piston rod 120, a ring-formed piston rod drive element 130, and a first element 140 defining a rotatable component that rotates together with the piston rod drive element 130 during expelling so that the first element 140 experiences unidirectional rotational movement relative to a second element 103 fixedly disposed within the housing 101.

The first element 140 defines a toothed wheel having a protrusion configuration comprising a plurality of serially disposed protrusions 143 protruding radially outwards. The protrusions are equally spaced along the circumference of first element 140. In FIG. 4, the first element 140 is configured for being driven in anti-clockwise direction only (seen from the push-button end of the device). Each protrusion 143 is formed with a gradually rising leading side and a sharply dropping trailing side. In the shown embodiment the protrusion configuration of the first element 140 defines protrusions being spaced with angular steps of 15 deg., meaning that twenty-four protrusions are distributed evenly around the circumference. Between any two neighbouring protrusions the first element defines a bottom level in the valleys, whereas the peaks of the protrusions 143 define a top level.

The second element 103 forms a generally tubular element formed to encircle the first element 140. The second element 103 has a first deflectable arm 103a and a second deflectable arm 103b, each deflectable arm extending in the circumferential direction. Each of the first and second deflectable arm 103a/103b includes at its free end a tip portion 103a'/103b' having a radially inwards pointing first surface which is angled to be generally parallel with a gradually rising side of a protrusion. Each tip portion 103a'/103b' further has a second surface which is angled to be generally parallel with the sharply dropping side of a protrusion 143.

The radially inwards pointing first surface of the tip portions 103a'/103b' is configured to ride over consecutive protrusions 143 as the first element 140 rotates relative to the second element 103 so that the tip portions 103a'/103b' of the first and second deflectable arm 103a/103b remain in intimate contact with the outer contour of the first element 140 including the valleys between protrusions.

In the shown embodiment, each of the first and second deflectable arms 103a/103b connects to the second element 103 by a reduced resilient portion 103a"/103b" so that the deflectable arms 103a/103b are radially movable from a relatively unbiased radial first position when the respective tip portion 103a'/103b' is located between neighbouring protrusions 143, i.e. at the bottom level, and into a biased radial second position when the respective tip portion 103a'/103b' is located upon a top portion of a protrusion 143. The second element 103 will typically be formed from a polymeric material with the first and second deflectable arms 103a/103b being unitarily moulded with the remaining portion of the second element 103.

In the shown embodiment, the tip portion 103a' is located generally diametrically opposite from the tip portion 103b'. However, in accordance with the invention, the tip portions 103a' and 103b' are located on the second element 103 so that the tip portions 103a' and 103b', by cooperating with diametrically opposed protrusions 143 of the first element 140, will not assume the biased radial second position at the same time, but slightly offset from each other. In the shown embodiment, the tip portions 103a' and 103b' are located approximately 178 degrees apart so that, as the first element 140 rotates relative to the second element 103, the first deflectable arm 103a will experience cooperation with a particular first protrusion slightly before the second deflectable arm 103b will experience cooperation with a protrusion arranged diametrically opposite from the first protrusion.

Figure 9:
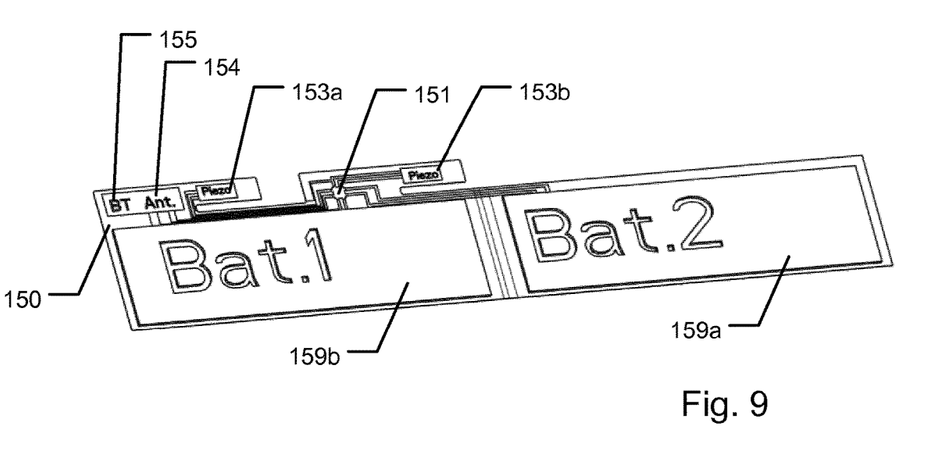
FIG. 9 is a flexible substrate with electronic circuitry of the first embodiment, the substrate including piezoelectric sensors.

In accordance with the invention, and referring to FIG. 9, in the shown embodiment, in order to monitor operation of the device by electronic means, an electronic circuitry 150 is disposed in or on the device 100 for registering events associated with operations performed by the device. The electronic circuitry will typically include a processor 151, an energy source 159, and a plurality of sensors 153a/153b for monitoring movements of one or more components within the drug injection device. In the shown embodiment, the electronic circuitry 150 also includes wireless communication means, e.g. antenna 154 and communication circuitry, such as Bluetooth unit, for communicating registered events to an external device, such as a Smartphone. Although not incorporated in the shown embodiment, the electronic circuitry may in other embodiments further include a display so as to offer a visible read-out of information related to registered events. In the shown embodiment, the electronic circuitry 150 is provided as a flexible sheet, such as a flexible electronic label, that includes printed circuitry including piezoelectric sensors 153a/153b printed onto the flexible sheet. In other embodiments, the electronic circuitry may be provided in other ways, e.g. with electronic components being disposed by other means than by printing.

Each of the first and second deflectable arms 103a/103b is configured to cooperate with a respective sensor 153a/153b to monitor deflection of the deflectable arms 103a/103b as the first element 140 rotates during expelling. In the shown embodiment each sensor is provided as an active transducer in the form of a piezoelectric element which is disposed on the respective deflectable arm 103a/103b by being adhered to the deflectable arm along its extension. Each piezoelectric element thus extends along the associated arm so that the generated activation signal from the piezoelectric element is representative for the degree of bending of the deflectable arm.

Figure 8:
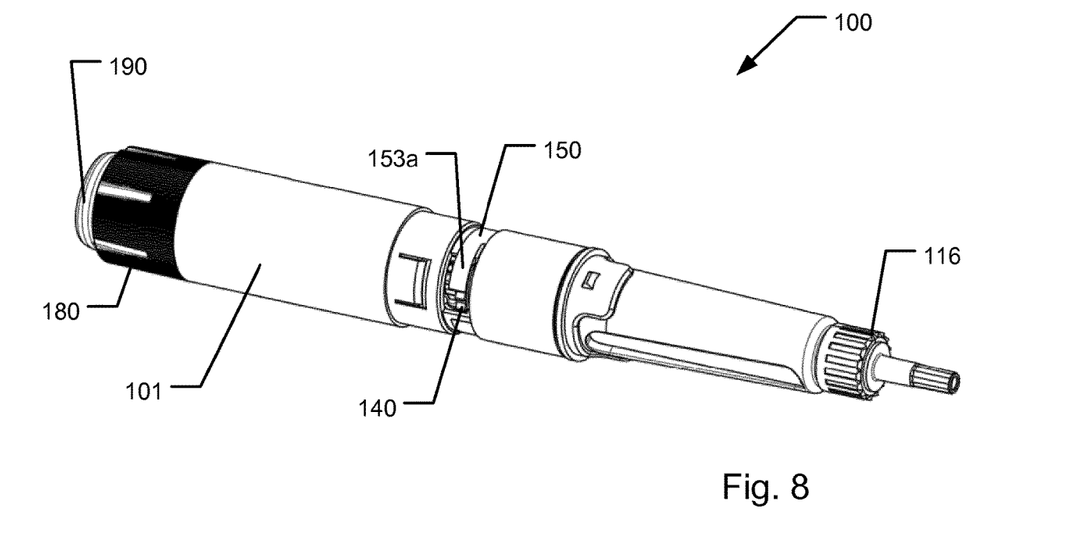
FIG. 8 is a perspective view of a pen device 100 of the first embodiment, the view being partly cut open revealing a portion of an electronic circuitry.

Reference is now made to FIG. 8 which shows a perspective view of pen injection device 100. For illustrative purposes FIG. 8 depicts the device 100 with a part of the housing 101 omitted so as to reveal details of the first element 140, and a portion of the electronic circuitry 150 including one sensor 153a associated with the deflectable arms 103a. Arranged within the part of the device facing away from the omitted housing portion and thus not visible in FIG. 8, the second deflectable arm 103b and one sensor 153b are located. In the shown embodiment, the electronic circuitry 150 is arranged in device 100 so that the flexible sheet encircles the second element 103 in a way where a first battery portion 159a and a second battery portion 159b are arranged in overlapping relationship, and so that the first piezoelectric element 153a aligns angularly with the first deflectable arm 103a. Also, the second piezoelectric element 153b aligns angularly with the second deflectable arm 103b. Although not shown, a further housing portion may be arranged to cover the electronic circuitry.

Figure 6:
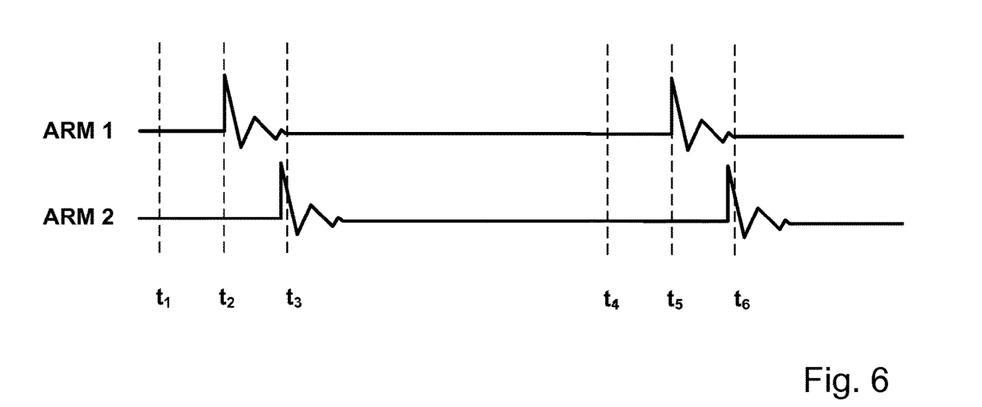
Figure 7:
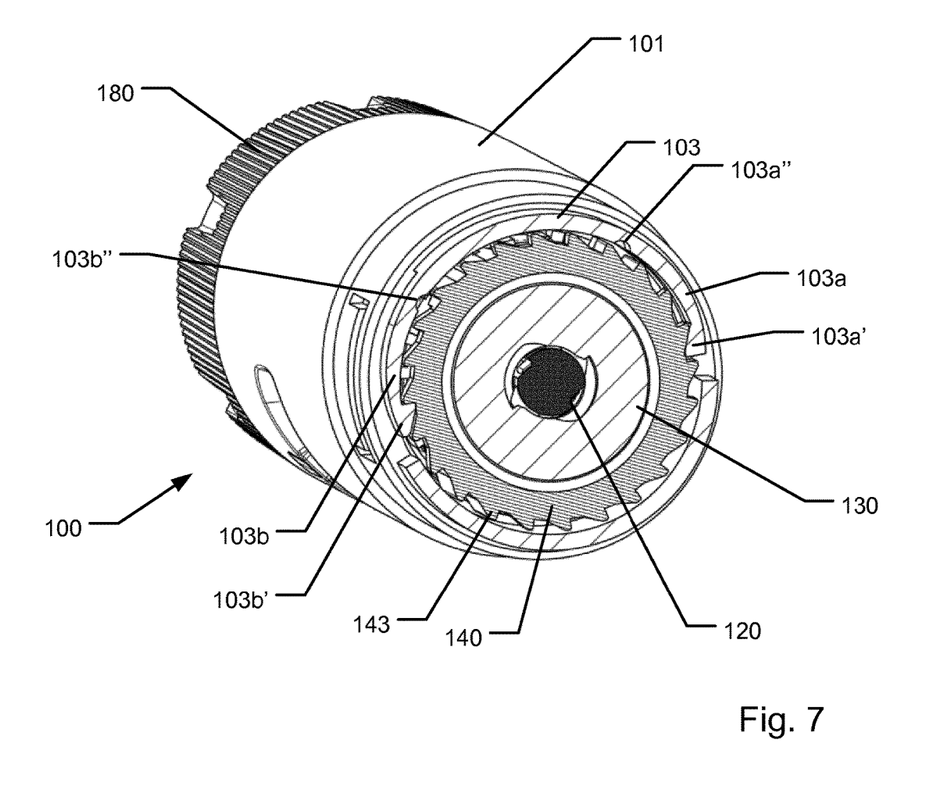
FIG. 7 is a perspective cross sectional view of a pen device 100 of a second embodiment according to the invention.

FIG. 6 shows schematically the voltage signal generated by the two piezo-electric sensors as the first element 140 rotates during expelling of a set dose, with the signal from the first piezoelectric sensor 153a referred to by the label "ARM 1" and the signal from the second piezoelectric sensor 153b referred to by the label "ARM 2". Each time the deflectable arm 103a passes the peak of a protrusion 143, so that the arm tip portion 103a' snaps into the next consecutive valley, this will generate a transient pulse having a large peak followed by damped ringing.

In the upper part of FIG. 6, the signal labelled "ARM 1" obtained by the first piezoelectric sensor 153a shows first and second individual pulses, at t=t1 and t=t5, respectively, being separated by a time interval with no pulses. The two pulses correspond to the tip portion 103a' of "ARM 1" cooperating with the peaks of two consecutive protrusions 143, or rather with the abruptly falling decline following each peak. In the shown embodiment, each of the two peaks corresponds to the expelling of an amount of one unit of drug contained in the cartridge.

As shown in the lower part of FIG. 6, the signal labelled "ARM 2" obtained by the second piezoelectric sensor 153b also shows first and second individual pulses, at t=t3 and t=t6, respectively, being separated by a time interval with no pulses. The two pulses correspond to the tip portion 103b' of "ARM 2" cooperating with the peaks of two consecutive protrusions 143, or rather with the abruptly falling decline following each peak.

Comparing the signals from "ARM 1" and "ARM 2" it is clear that during expelling of each unit of drug, a pulse is firstly registered by the first piezoelectric sensor 153a at t=t2, whereafter, within a short time delay, a corresponding pulse is registered by the second piezoelectric sensor 153b at t=t3. Hence, during expelling of consecutive units of drug, pairs of activation signals will be generated i.e. at (t=t2; t=t3), at (t=t5; t=t6) etc. by the first piezoelectric sensor 153a and the first piezoelectric sensor 153b respectively.

The time delay between pulses received by the first piezoelectric sensor 153a and the second piezoelectric sensor 153b is partly defined by the particular geometry of the protrusions 143 on the first element 140 and the position of the first and second deflectable arms 103a/103b on the second element 103, and partly determined by the rotational speed of the first element 140 during expelling. For a given design of the device 100 the manufacturer will be able to provide a range within which anticipated variations of time delays between pulses of the first piezoelectric sensor 153a and the second piezoelectric sensor 153b is likely to occur, the range corresponding to expelling procedures where registered movements are reliable and correct. In accordance herewith, the manufacturer will be able to determine a pre-defined value of a minimum time delay which is deemed to correspond to a correct and reliable sequence of activations signals generated from the first piezoelectric sensor 153a and the second piezoelectric sensor 153b. If a registered time delay, as registered by signals generated by the first piezoelectric sensor 153a and the second piezoelectric sensor 153b, is above or equal to the pre-defined value, the pulses may be registered and counted so as to provide a measure of the quantity expelled from the device 100.

If registered time delays are below said pre-defined value, this may signify an error. Such error may for example occur during handling or transportation if the device is unintentionally dropped on a hard surface. This will typically generate a large impact on the device, and the first piezoelectric sensor 153a and the second piezoelectric sensor 153b may generate activation signals in response to the impact, even though the first element 140 is not rotating. However, the impact will typically make the first piezoelectric sensor 153a and the second piezoelectric sensor 153b generate activation signals almost simultaneously, i.e. so that a possible registered time delay between the activation signals will be below the pre-defined value.

The processor 151 will typically be configured to provide a) a first control action if a time delay determined by the processor is above or equal to a pre-defined value, and b) a second control action if a time delay determined by the processor is below the pre-defined value.

In certain embodiments, the processor comprises a counter adapted to count the number of units expelled from the device. The counter may in one embodiment use information from the first piezoelectric sensor 153a to count expelled units. Alternatively, the counter may use information from the second piezoelectric sensor 153b to count expelled units. In the shown embodiment, the processor is configured to modify a value of the counter upon performing the first control action, and configured not to modify the value of the counter upon performing the second control action.

The processor typically includes circuitry to keep track of time. In this way a log may be provided in a storage of the electronic circuitry so that the quantity of an expelled dose is stored together with a time parameter, such as a real-time value, or a relative time-stamp. A plurality of individual sets of stored quantities of expelled drug and associated time values may be stored for later retrieval. In the shown embodiment, the contents of the storage, i.e. the log, may be transferred to an external device.

In other embodiments, the processor may not include a counter as such to keep track of quantities of expelled doses. In such configurations, the processor may alone be configured to register when an expelling operation is performed and to store the occurrence of an expelling operation together with a time stamp.

In other embodiments, the principle of using a sensor configuration providing a pair of activation signals with a time-delay between the pair and within a pre-defined range may be utilized for monitoring movement of other components within the injection device than the described component moving during expelling. For example, instead or in addition to the described monitoring of a component that moved during expelling, a component that moves during dose setting may be monitored using the same principle.

Also, the shown configuration of a pair of deflectable arms cooperating with one and the same track of protrusions is only an example of a suitable configuration. In alternative configurations, each deflectable arm may cooperate with a respective one of two individual tracks of protrusions. For example, the first element may be provided as a cylindrical element having a first track of protrusions arranged facing radially outwards and a second track of protrusions arranged facing radially inwards, so that each deflectable arm cooperates with a respective one of the first and second tracks. In still other embodiments, the first element may include protrusion configurations on one or both axial facing end walls that cooperate with dedicated deflectable arms.

In still other embodiments, the described principle of monitoring movement may be used to monitor a linearly moved component in the device.

The invention claimed is:
1. A drug injection device comprising:
a first element and a second element configured to undergo movement relative to each other, said movement being a unidirectional movement in a first direction corresponding to an action performed on or by the drug injection device and representing an amount of drug delivered, or to be delivered, from the drug injection device,
wherein the first element comprises a protrusion configuration comprising a plurality of serially disposed protrusions equally spaced along the first direction of movement,
wherein the second element comprises first and second deflectable transducers, each of the first and the second deflectable transducers being configured for sequentially cooperating with the plurality of protrusions of the first element to become deflected thereby generating an activation signal as each of the first and the second deflectable transducers is deflected when travelling past each of the plurality of protrusions, and
a processor electrically connected with the first and second deflectable transducers to register generated activation signals from the first and second deflectable transducers, and being configured to determine, from the registered activation signals, an amount of drug delivered or to be delivered from the drug injection device,
wherein
the protrusion configuration is so disposed on the first element and the first and second deflectable transducers are so disposed on the second element so that a second activation signal generated by the second deflectable transducer is delayed relative to a first activation signal generated by the first deflectable transducer as the first element and the second element move relative to each other,
wherein the processor is configured to register the first activation signal and the second activation signal and to determine a time delay there between, and
wherein the processor is configured to provide a) a first control action if said time delay is above or equal to a pre-defined value, and b) a second control action if said time delay is below said pre-defined value.

2. The drug injection device according to claim 1, wherein each of the first and second deflectable transducers comprises a deflectable portion arranged to become deflected in a direction generally transverse to the first direction by cooperating with the plurality of protrusions of the protrusion configuration.

3. The drug injection device according to claim 1, wherein each of the first and the second transducers comprises a respective deflectable arm defined by a resiliently deflectable polymeric or metallic material portion configured to become deflected in a direction generally transverse to the first direction upon cooperating with the plurality of protrusions of the protrusion configuration.

4. The drug injection device according to claim 3, wherein engaging geometries of the plurality of protrusions of the protrusion configuration and the deflectable arm of the first and/or the second deflectable transducers defines a click mechanism that generates audible clicks as the plurality of protrusions pass the deflectable arm of the first and/or the second deflectable transducers.

5. The drug injection device according to claim 3, wherein, for each of the first and the second deflectable transducer, engaging geometries of the plurality of protrusions of the protrusion configuration and the respective deflectable arm of the first and the second deflectable transducers is configured to provide a gradually rising deflection of the deflectable arm into a biased state followed by an abrupt release from the biased state as each of the plurality of protrusions passes the respective deflectable arm of each of the first and the second deflectable transducers.

6. The drug injection device according to claim 1, wherein the drug injection device defines a ratchet mechanism between the first element and the second element so as to prevent relative movement between the first element and the second element in a direction opposite to said first direction.

7. The drug injection device according to claim 1, wherein the first element and the second element are arranged co-axially along a central axis, the first element and/or the second element being rotationally movable around the central axis for relative rotational movement in a first rotational direction.

8. The drug injection device according to claim 7, wherein the first element defines a circular element having the plurality of protrusions evenly arranged in an angular direction and wherein the plurality of protrusions are arranged to protrude radially for radially deflecting the first and the second deflectable transducers.

9. The drug injection device according to claim 7, wherein the first and the second deflectable transducers are disposed in a generally symmetrical configuration around the central axis.

10. The drug injection device according to claim 1, wherein the plurality of serially disposed protrusions of the first element are equally spaced with a distance S, and wherein the first and second deflectable transducers are positioned on the second element so that the second activation signal from the second deflectable transducer (103b/153b) and the first activation signal from the first deflectable transducer are generated within a relative movement between the first element and the second element corresponding to less than 0.5 times S, more preferably less than 0.4 times S, more preferably less than 0.3 times S, and most preferably less than 0.2 times S.

11. The drug injection device according to claim 1, wherein the processor comprises a counter and wherein the processor is configured to modify a value of the counter upon performing the first control action, and configured not to modify the value of the counter upon performing the second control action.

12. The drug injection device according to claim 1, wherein the first and/or the second deflectable transducers are provided as, or comprises, one of a piezoelectric sensor, a strain gauge, a galvanic foil sensor, and a capacitive sensor having an elastic dielectric between two electrodes.

13. The drug injection device according to, claim 1 wherein the first and/or the second deflectable transducers comprise a printed piezoelectric material.

14. The drug injection device according to claim 1, wherein the first and the second deflectable transducers and the processor are arranged on a flexible sheet.

15. The drug injection device according to claim 1, wherein the drug injection device defines a housing extending along a longitudinal axis, and further comprises a drug expelling mechanism for expelling a volume of drug from a reservoir, wherein the first element and/or the second element form part of the drug expelling mechanism, and wherein the relative unidirectional movement between the first element and the second element about the longitudinal axis is provided during a drug expelling action in accordance with an expelled dose.

* * * * *